United States Patent
Kleber et al.

(10) Patent No.: US 6,653,112 B2
(45) Date of Patent: *Nov. 25, 2003

(54) METHOD FOR PRODUCING L-CARNITINE FROM CROTONOBETAINE USING A TWO STAGE CONTINUOUS CELL-RECYCLE REACTOR

(75) Inventors: Hans-Peter Kleber, Grossdeuben (DE); Manuel Canovas-Diaz, Santo Angel-Murcia (ES); Jose Maria Obon, Murcia (ES); Jose Maria Iborra, Murcia (ES)

(73) Assignee: Sigma-Tau Industrie Farmaceutiche Riunite S.p.A., Rome (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/530,783

(22) PCT Filed: Nov. 9, 1998

(86) PCT No.: PCT/EP98/07124

§ 371 (c)(1),
(2), (4) Date: May 12, 2000

(87) PCT Pub. No.: WO99/24597

PCT Pub. Date: May 20, 1999

(65) Prior Publication Data

US 2003/0073203 A1 Apr. 17, 2003

(30) Foreign Application Priority Data

Aug. 11, 1997 (DE) .......................... 197 49 480

(51) Int. Cl.[7] .......................... C12P 13/00; C12P 7/40; C12N 11/14; C12N 11/08; C12N 1/20
(52) U.S. Cl. .................. 435/128; 435/136; 435/176; 435/180; 435/252.8; 435/280; 435/849
(58) Field of Search ................. 435/128, 174, 435/176, 180, 136, 280, 252.8, 849

(56) References Cited

U.S. PATENT DOCUMENTS

| 4,906,568 A | * | 3/1990 | Jung et al. | 435/128 |
|---|---|---|---|---|
| 4,978,616 A | * | 12/1990 | Dean, Jr. et al. | 435/70.3 |
| 5,028,538 A | * | 7/1991 | Seim et al. | 435/128 |

FOREIGN PATENT DOCUMENTS

EP 0 320 460 6/1989

OTHER PUBLICATIONS

Jung, et. al., Chemical Abstracts 117: 187989 d, 1992.*
Jung, et. al., Chemical Abstracts 115: 6956 f, 1991.*
Trevan, et. al., Immobilized Enzymes, John Wiley & Sons 1980, pp. 66–71.*

* cited by examiner

*Primary Examiner*—David M. Naff
(74) *Attorney, Agent, or Firm*—Nixon & Vanderhye P.C.

(57) ABSTRACT

L(–)-carnitine is synthesized from crotonobetaine, crotonobetaine salts or derivatives in an ecologically advantageous manner by immobilizing cells of *Escherichia coli* 044 K74 on ceramics, glass beads or polyurethane disks in a two stage continuously operating cell recycle reactor containing a reaction medium. The medium preferably contains between 25 mM and 1 M crotonobetaine and at least 50 mM fumarate. Growing or resting cells of *E. coli* are retained in the reactor by micro or ultrafiltration membranes which are arranged as a flat membrane module or hollow fiber module. A first stage contains a reactor tank and a second stage contains an external recirculation loop connected to the tank for feeding the reaction medium through a filter unit. L-carnitine is synthesized under anaerobic conditions to produce a reaction medium containing L-carnitine and unreacted crotonobetaine. The reaction medium is transferred through the recirculation loop to the filter unit to produce a filtrate containing L-carnitine and a residue containing unreacted crotonobetaine and cells. The residue is recirculated to the reactor tank.

9 Claims, No Drawings

METHOD FOR PRODUCING L-CARNITINE FROM CROTONOBETAINE USING A TWO STAGE CONTINUOUS CELL-RECYCLE REACTOR

FIELD OF THE INVENTION

The invention relates to a process for producing L-carnitine from crotonobetaine, from salts of crotonobetaine, other derivatives of crotonobetaine or the like.

BACKGROUND OF THE INVENTION

It is known that L-carnitine, a ubiquitously occurring compound, plays an important role in metabolism, especially in transporting long-chain fatty acids through the inner mitochondrial membrane. Numerous clinical applications derive from the function of carnitine in the metabolism of eukaryotes, e.g., in the treatment of patients with carnitine deficiency syndromes, in the prevention and therapy of various heart diseases and in the treatment of hemodialysis patients. Further, L-carnitine is significant as a supplemental nutrient and also promotes, as an additive to fermentation media, the growth of yeasts and bacteria. The growing need for this biologically active L-carnitine enantiomer for these and other applications has led to a worldwide search for means of synthesizing this betaine in an optically pure form, since the chemically synthesized racemate cannot be used because it inhibits carnitine acetyl transferase and the carnitine carrier protein.

To isolate the L-isomer, up to now processes have been used that are based on splitting racemates by fractionated crystallization using optically active acids (e.g., U.S. Pat. No. 4,254,053, 1981), where D(+)-carnitine occurs as a waste product.

This problem can be overcome by various biological processes, starting with inexpensive achiral precursors (Adv. Biochem. Eng. Biotechnol., 1993, 50, 21–44) Of particular interest is stereospecific hydration of trans-crotonobetaine into L-carnitine using strains of the genera Escherlchia (ED 0121444, 1984; DD 221 905, 1987; EP 0320460, 1989) or Proteus (Agric. Biol. Chem., 1988, 52, 2415–2421; U.S. Pat. No. 5,300,430, 1994) The advantage of this method lies in the fact that this achiral precursor can also be obtained by chemical dehydration of the waste product D-carnitine.

The numerous processes described in the literature with immobilized microorganisms in a continuously operating reactor system have the advantage that

- pure reaction media can be used, thus facilitating the extraction and purification process,
- by using higher concentrations of the biocatalyst in the reaction medium, higher productivities are achieved while the possibility of contamination is reduced,
- there is reduced sensitivity to inhibitors or a nutrient deficiency,
- a higher stability of the biocatalyst is achieved.

The advantages mentioned can also be applied to a commercially used process.

A continuously operating reactor in which microorganisms are retained by micro- or ultrafiltration membranes is an immobilization process which, besides the above-mentioned advantage, also entails lower costs for the immobilization while making it possible to have a very slight upscaling.

SUMMARY OF THE INVENTION

Consequently the object of the invention is a process for producing L-carnitine from crotonobetaine, crotonobetaine salts or other crotonobetaine derivatives in a continuous reactor with free or immobilized cells, growing or resting *Escherlchla coil* 044K74 (DSM 8828) cells, that are retained by micro- or ultrafiltration membranes in a flat membrane or hollow fiber module.

DETAILED DESCRIPTION OF THE INVENTION

*E. coil* is kept in the reactor mentioned at temperatures between 20 and 40° C., pH values between pH 6.0 8.0 and under anaerobic conditions that are necessary for the induction of the enzyme that metabolizes carnitine.

A minimal or complex medium is used as the reaction medium. In both cases, crotonobetaine, crotonobetaine salts or other crotonobetaine derivatives are added in concentrations between 25 mmol and 1M. The minimal medium contains varying concentrations of caseine hydrolyzate and salts $(NH_4)_2SO_4$, $KH_2PO_4$, $K_2HPO_4$, $MgSO_4x7H_2O$, $MnSO_4x4H_2O$, $FeSO_4x7H_2O$, while the complex medium contains varying concentrations of pancreatic peptone and NaCl. To improve the growth of *E. coil*, glycerine, glucose, ribose, saccharose or lactose are added. Also added to the medium are inhibitors that prevent the transformation of crotonobetaine into y-butyrobetaine (fumarate, glucose or nitrate) and inductors of carnitine-metabolizing enzymes such as D-, L-, DL-carnitine, their salts and derivatives or crotonobetaine, its salts or derivatives.

The course of the reaction in the continuous cell-recycle reactor used here can be divided into two stages. The one stage consists of a reactor tank in which cells of *E. coil*, together with the reaction medium, convert most of the crotonobetaine into L-carnitine. This reactor tank has monitoring elements for pH value, temperature and stirring speed and for the monitoring and correction of oxygen concentration. The feed of the reaction medium into the reactor is performed with a dosing pump. When necessary, excess medium must be removed from the reactor tank. The second stage consists of an external recycling loop that is connected to the reactor tank and conveys the contents of the reactor through a filter unit by means of a pump. While the filtrate is being collected, to isolate L-carnitine from it as the reaction product, the residue from the filtration is fed again to the reactor. For filtering the cell suspension, commercial filter systems of varying provenance can be used as long as they have a pore size below the cell size of *E. coil*. The speed of the recycling pump remains unchanged to achieve the best possible filtration rates and to minimize the formation of a polarization membrane during the filtration process. Filtering may be performed using commercial cross current filtration or hollow-fiber modules consisting of ultra-or microfiltration membranes composed of cellulose, polysulphone or polysulphonated polysulphone with a retention limit of 300 kDa or 0.211 $\mu$. The continuous cell-recycle reactor may be operated at different levels of dilution adjusted by dosing and filtration pumps, and at different agitation speeds and different biomass concentrations. Rate of discharge from the filtration pump is controlled by process control means.

The expression free *E. coil* cells indicates the state in which whole cells are suspended in the reaction medium without preventing a cell outflow through the exit solution. The expression immobilized cells describes the state in which whole cells are bonded to soluble polymers or insoluble carriers, or are enclosed in membrane systems (in Methods in Enzymol. 1987, vol. 135, 3–30)

The concept growth conditions is defined as the situation in which whole cells use substrates and form products during their life cycle. Resting cells are understood as intact cells that are not growing and that show, under certain conditions, special metabolic functions (in "Biotechnology" (Kieslich, K.; Eds. Rehm, N.J. and Reed, G.) Verlag Chemie, Weinheim, Germany. 1984, Vol. 6a, 5–30)

The process is described below with several embodiments:

EXAMPLE 1

*Escherlchla coil* 044 K74 is cultivated in an Erlenmeyer flask that is filled to the top and sealed air-tight at 37° C. under anaerobic conditions, on a rotating shaker (150 r.p.m.). The complex medium used has the following composition: 50 mM of crotonobetaine, 50 muM fumarate, 5 g/l of NaCi and varying concentrations (between 0.5 and 10 g/l) of pancreatic peptone. The pH is set using KOH to pH 7.5. Table 1 summarizes the specific growth rates at varying peptone concentrations.

TABLE 1

Maximum specific growth rates of *Escherlchla coil* 044 K74

| Peptone (g/l) | 0.5 | 1.0 | 2.5 | 5.0 | 10.0 |
|---|---|---|---|---|---|
| pmax (h~) | 0.224 | 0.296 | 0.351 | 0.372 | 0.325 |

Under the conditions described, growing cells of *E. coli* are able to produce 20–30 mM of L-carnitine up to the end of the test.

Concentrations higher than 5 g/l of peptone yield similar growth and kinetic parameters as well as biomass content (OD 600 nm) In contrast, at lower peptone concentrations, lower growth parameters are obtained.

EXAMPLE 2

*Escherlchla coil* 044 K74 is cultivated in an Erlenmeyer flask that is filled to the top and sealed air-tight at 37° C. under anaerobic conditions, on a rotating shaker (150 r.p.m.) The complex medium used has the following composition: 50 muM of crotonobetaine, 5 g/l of pancreatic peptone, S g/l of NaCl and graduated concentrations (between 0 and 75 muM) of fumarate. The pH is set using KOR to pH 7.5.

Table 2 shows that adding fumarate causes higher growth rates of *E. coli* 044 K74 and an OD of 600 nm of almost 1.0 in the steady state. Further, fumarate causes L-carnitine formation of 20–30 muM up to the end of the test. In the absence of fumarate, a carnitine concentration of only 5 muM is obtained.

TABLE 2

Biomass ($0D_{600}$~) at varying fumarate concentrations after a 10 hour test.

| Fumarate (mM) | 0 | 25 | 50 | 75 |
|---|---|---|---|---|
| ~max ($h^1$) | 0.21 | 0.37 | 0.38 | 0.39 |
| Biomass OD (600 nm) | 0.980 | 0.910 | 1.00 | 0.950 |

EXAMPLE 3

The ability of *Escherlchla coil* 044 K74 to form L-carnitine from crotonobetaine is induced by crotonobetaine. The induction studies were performed with crotonobetaine between 5 and 75 muM using resting cells. At higher crotonobetaine concentrations, conversion rates of above 60% of L-carnitine are achieved (Table 3)

TABLE 3

Production of L-carnitine by resting cells of *Escherlchla coil* 044 K74 as a function of varying crotonobetaine concentrations.

| Crotonobetaine (mM) | 5 | 25 | 50 | 75 |
|---|---|---|---|---|
| L-carnitine production (%) | 55 | 60 | 62 | E5 |

EXAMPLE 4

*Escherlchla coil* 044 K74 is cultivated in an Erlenmeyer flask that is filled to the top and sealed air-tight at: 37° C. under anaerobic conditions, on a rotating shaker (150 r.p.m.). The complex medium used has the following composition: 50 mM of crotonobetaine, 5 g/l of pancreatic peptone, 5 g/l of NaCl and 50 mM of fumarate. The pH is set using KON to pH 7.5.

To raise the biocatalyst concentration in the reactor and to make it possible to have L-carnitine production at dilution rates higher than the maximum specific growth rate, a membrane reactor was used. The cells were retained with a polysulfone microfiltration membrane with an exclusion threshold of 0.1 pm and were used again. The membranes were arranged in a plate module. Table 4 summarizes the biomass content and Table 5 summarizes the carnitine production, the crotonobetaine conversion and the productivity in this system.

TABLE 4

Biomass content of *E. coil* 044 K74 in a continuously operating membrane reactor.

| Dilution rate ($h^1$) | 0.0 | 0.2 | 1.0 | 2.0 |
|---|---|---|---|---|
| Biomass (gdryweight/1) | 0.5 | 2.1 | 9.4 | 27.0 |

TABLE 5

L-carnitine production, crotonobetaine conversion and productivity in a continuously operating cell reactor wlih *Escherlchla coil* 044 K74

| Dilution rate ($tf^1$) | 0.0 | 0.5 | 1.0 | 1.5 | 2.0 |
|---|---|---|---|---|---|
| L-carnitine production (%) | 0.0 | 38 | 42 | 42 | 38 |
| Crotonobetaine conversion (%) | 0.0 | 24 | 26 | 26 | 30 |
| Productivity | 0.0 | 1.75 | 3.5 | 5.5 | 6.5 |

It can be seen from the tables that, with immobilized cells of *Escherlchla coil* 044 K74 in a cell recycle reactor, 6.5 1/h of L-carnitine was formed from crotonobetaine with a metabolization rate of almost 40%.

What is claimed is:

1. A method for producing L-carnitine from crotonobetaine, comprising the steps of:
    (1) introducing between 25 mM and 1 M crotonobetaine or a salt or derivative thereof and at least 50 mM fumarate into a reaction a two stage continuously operating cell-recycle reactor wherein a first stage consists of a reactor tank containing the reaction medium and cells of a strain of the genera Escherichia that convert crotonobetaine to L-carnitine, said cells being immobilized on a carrier selected from ceramics, glass beads and polyurethane disks, and a second stage consists of an external recirculation loop connected to the reactor tank, by means of which the contents of the reactor are fed through a filter unit;

(2) synthesizing the L-carnitine under anaerobic condition in the reaction medium containing fumarate and crotonobetaine to produce a reaction medium containing L-carnitine and unreacted crotonobetaine; and (3) transferring said reaction medium through the recirculation loop to said filter unit where the reaction medium is filtered to produce a filtrate containing the L-carnitine from the reaction medium and recirculating from the filter unit a residue containing unreacted cronobetaine into the reactor tank of step (1).

2. A method according to claim 1, wherein the cells are *E. coli* 044 K74 (DSM 8828).

3. A method according to claim 2, wherein the carrier does not impair viability of the cells.

4. A method according to claim 1, wherein the cells are immobilized on ceramics.

5. A method according to claim 2, wherein the reaction medium contains 50 mM crotonobetaine, 5 g/l pancreatic peptone, 5 g/l NaCl and 50 mM fumarate, has a pH of 7.5, and the cell-recycle reactor comprises a continuously operating membrane reactor.

6. A method according to claim 1, wherein in step (3) the residue contains the cells and the cells are continuously recycled to the reactor tank, and the reaction medium is filtered by cross-flow filtration or hollow fiber modules consisting of ultra- or microfiltration membranes.

7. A method according to claim 6, wherein the membranes are composed of cellulose, polysulphone or polysulphonated polysulphone with a retention limit of 300 kDa or $0.211\mu$.

8. A method according to claim 1, wherein the cell-recycle reactor is operated at different levels of dilution which are adjusted by a dosing pump and a filtration pump, and at different agitation speeds and different biomass concentrations.

9. A method according to claim 8, wherein a rate of discharge of the filtration pump is controlled by process control means.

* * * * *

UNITED STATES PATENT AND TRADEMARK OFFICE
CERTIFICATE OF CORRECTION

PATENT NO. : 6,653,112 B2
DATED : November 25, 2003
INVENTOR(S) : Kleber et al.

It is certified that error appears in the above-identified patent and that said Letters Patent is hereby corrected as shown below:

Title page,
Item [30], Foreign Application Priority Data, should read
-- November 8, 1997    (DE) ............................. 197 49 480 --

Signed and Sealed this

Twenty-fifth Day of May, 2004

JON W. DUDAS
*Acting Director of the United States Patent and Trademark Office*